United States Patent
Buttner et al.

[11] 3,932,406
[45] Jan. 13, 1976

[54] 2-TRIFLUOROMETHYLIMINO-1,3-DITHIOLO[4,5-b]-QUINOXALINES

[75] Inventors: Gerhard Buttner, Cologne; Klaus Sasse, Schildgen; Ingeborg Hammann, Cologne; Helmut Kaspers, Leverkusen, all of Germany

[73] Assignee: Bayer Aktiengesellschaft, Leverkusen, Germany

[22] Filed: Apr. 23, 1974

[21] Appl. No.: 463,642

[30] Foreign Application Priority Data
May 4, 1973 Germany............................ 2322434

[52] U.S. Cl............................ 260/250 Q; 424/250
[51] Int. Cl.²........................................ C07D 495/04
[58] Field of Search..................... 260/250 Q, 250 R

[56] References Cited
UNITED STATES PATENTS

| | | | |
|---|---|---|---|
| 3,029,238 | 4/1962 | Sasse et al. | 260/250 Q |
| 3,091,613 | 5/1963 | Sasse et al. | 260/250 Q |
| 3,141,886 | 7/1964 | Sasse et al. | 260/250 Q |
| 3,223,706 | 12/1965 | Sasse et al. | 260/250 Q |

OTHER PUBLICATIONS
Sasse et al., Chemical Abstract 57: 12507f to 12509e at 12509c.

*Primary Examiner*—Raymond V. Rush
*Assistant Examiner*—Mark L. Berch
*Attorney, Agent, or Firm*—Burgess, Dinklage & Sprung

[57] ABSTRACT

2-Trifluoromethylimino-1,3-dithiolo[4,5-b]-quinoxalines of the formula

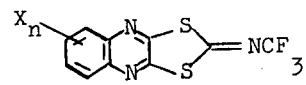

in which

X is lower alkyl, lower alkoxy, trihalogeno-methyl, trihalogenomethoxy, halogen or nitro, and n is an integer from 0 to 4, which possess insecticidal, acaricidal, fungicidal and nematocidal properties.

7 Claims, No Drawings

2-TRIFLUOROMETHYLIMINO-1,3-DITHIOLO [4,5-b]-QUINOXALINES

The present invention relates to and has for its objects the provision of particular new 2-trifluoromethylimino-1,3-dithiolo[4,5-b]-quinoxalines substituted with alkyl, alkoxy, trifluoromethyl, trifluoromethoxy, nitro or halogen, which possess insecticidal, acaricidal, fungicidal or nematocidal properties, active compositions in the form of mixtures of such compounds with solid and liquid dispersible carrier vehicles and methods for producing such compounds and for using such compounds in a new way especially for combating pests, e.g. insects, acarids, fungi and nematodes, with other and further objects becoming apparent from a study of the within specification and accompanying examples.

It has been disclosed in German Published Specifications DAS 1,088,965 and 1,100,372 that acylation products of 2,3-dimercaptoquinoxaline or its nuclear-substituted derivatives can be employed for combating phytopathogenic fungi and various insects, especially spider mites. However, notwithstanding their good fungicidal and acaricidal properties, these compounds display only a slight insecticidal activity. Furthermore, their possible use is restricted because their plant tolerance is not always adequate.

The present invention provides, as new compounds, the 2-trifluoromethylimino-1,3-dithiolo[4,5-b]-quinoxalines of the formula

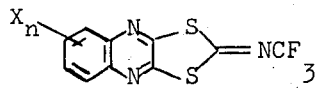

in which

X is lower alkyl, lower alkoxy, trihalogenomethyl, trihalogenomethoxy, halogen or nitro, and n is an integer from 0 to 4.

Preferably n is 0, 1 or 2; and X is fluorine, chlorine, nitro, or alkyl or alkoxy of up to 4 carbon atoms, e.g. methyl or methoxy.

Surprisingly, the 2-trifluoromethylimino-1,3-dithiolo-[4,5-b]-quinoxalines according to the invention, while exhibiting fungicidal activity as good as 2-phenylimino-1,3-dithiolo-[4,5-b]-quinoxaline (Compound A), which is chemically the nearest known compound of analogous type of activity, display a better insecticidal and acaricidal action and better tolerance by plants. The compounds according to the invention thus represent an enrichment of the art.

The present invention also provides a process for the preparation of a compound of the formula (I) in which an optionally nuclear-substituted 2,3-dimercaptoquinoxaline of the general formula

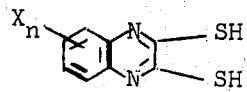

in which

X and n have the above-mentioned meanings, or a salt thereof, is reacted, in the presence of a hydrogen-fluoride acceptor, with perfluoroazapropene, of the formula

 (III)

in the presence of an inert solvent or diluent.

If 6-methyl-2,3-dimercapto-quinoxaline and perfluoroazapropene are used as starting materials and sodium fluoride as the acid-binding agent, the course of the reaction can be represented by the following equation:

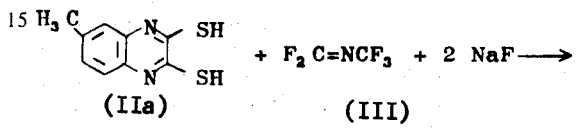

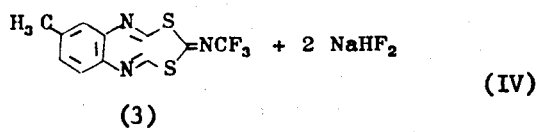

The compounds of the general formula (II) are known and can be prepared according to German Published Specifications DAS 1,088,965 and 1,100,372.

The following may be mentioned as examples of the starting compounds (II): 2,3-dimercaptoquinoxaline, 5-methyl-2,3-dimercaptoquinoxaline, 6-methyl-2,3-dimercaptoquinoxaline, 5,7-dimethyl-2,3-dimercaptoquinoxaline, 6-trifluoromethyl-2,3-dimercaptoquinoxaline, 6-methoxy-2,3-dimercaptoquinoxaline, 5-chloro-2,3-dimercaptoquinoxaline, 6-chloro-2,3-dimercaptoquinoxaline, 6,7-dichloro-2,3-dimercaptoquinoxaline, 5,7-dichloro-2,3-dimercaptoquinoxaline and 6-nitro-2,3-dimercaptoquinoxaline.

The perfluoroazapropene of the formula (III) to be used as a starting compound is also known (see Chem. Rev. 65, 387 (1965); and J. chem. Eng. Data 10, 398 (1965)).

Possible diluents are all inert organic solvents, such as hydrocarbons, for example toluene; halogenated hydrocarbons, for example methylene chloride, carbon tetrachloride, tetrachloroethylene or chlorobenzene; or ethers, for example diethyl ether, dioxane or tetrahydrofuran; but preferred are dipolar aprotic solvents, such as acetone, acetonitrile, dimethylformamide, dimethylacetamide, sulfolane or dimethylsulfoxide.

Acid-binding agents such as alkali metal carbonates, alkali metal fluorides, preferably sodium fluoride, and tertiary aliphatic or aromatic amines, such as trialkylamines, (especially triethylamine), pyridine or dimethylbenzylamine, can be used as acceptors for the hydrogen fluoride liberated in the reaction.

The reaction temperatures are in general between −20°C and +100°C, preferably between 0° and 80°C.

The process according to the invention can be carried out by dissolving 1 mole of starting material of the general formula (II) in dry dimethylformamide, acetone, acetonitrile or toluene, adding 2 moles of dry sodium fluoride or triethylamine and passing 1 to 1.5 moles, preferably 1.1 moles, of perfluoroazapropene, from a steel cylinder, slowly into this suspension, in the temperature range indicated, while stirring. After completion of the reaction the mixture is stirred for a little while longer and is worked up as appropriate to the solvent used. In the case of aprotic solvents the mixture is filtered and the solvent is concentrated in vacuo.

In the case of dipolar aprotic solvents the reaction mixture is poured into ice-water while stirring. The precipitate formed is filtered off, dried and, if necessary, purified by recrystallization.

The compounds according to the invention possess marked activity against acarids, as well as against phytopathogenic fungi, in addition to a good insecticidal activity, for example against sucking and biting insects. In addition, they are both fungicidally active (for example, against powdery mildew fungi) and microbistatically active. Some of the compounds of the present invention are also nematocidally active.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug, (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (*Lepidoptera*) such as the diamind-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia Kuhniella*) and greater wax moth (*Galleria mellonella*).

Also to be classed with the biting insects are beetles (*Coleoptera*), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed in particular, the spider mites (Tetranychidae) such as the two-spotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carriers vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, fungicides and nematocides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commerically marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application of field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids, fungi and nematodes, and more particularly methods of combating at least one of insects, acarids and fungi, which comprises applying to at least one of correspondingly (a) such insects, (b) such acarids, (c) such fungi, (d) such nematodes and (e) the corresponding habitat thereof, i.e. the locus to be protected, a correspondingly combative or toxic amount, i.e. an insecticidally, acaricidally, fungicidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpectedly superiority and outstanding activity of the particular new compounds of the present invention are illustrated, without limitation, by the following examples:

EXAMPLE 1

Tetranychus Test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained is expressed as a percentage: 100% means that all the spider mites were killed, whereas 0% means that none of the spider mites were killed.

The active compounds, the concentrations, by weight, of the active compounds, the evaluation times and the results can be seen from the following table:

TABLE 1
| Active compounds | | Mites which damage plants) Tetranychus test (resistant) | |
|---|---|---|---|
| | | Active compound concentration in % | Degree of destruction in % after 8 days |
| 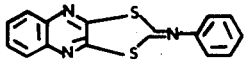 (known) | (A) | 0.1<br>0.01 | 40<br>0 |
| 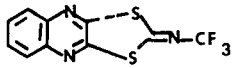 | (2) | 0.1<br>0.01<br>0.001 | 100<br>100<br>40 |
| 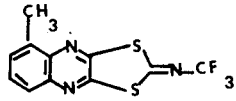 | (4) | 0.1<br>0.01<br>0.001 | 100<br>100<br>40 |
| 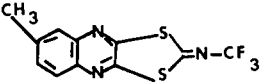 | (3) | 0.1<br>0.01<br>0.001 | 100<br>100<br>70 |
| 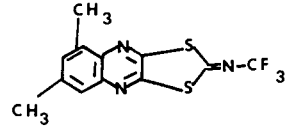 | (5) | 0.1<br>0.01 | 98<br>20 |
| 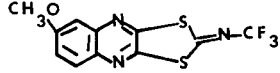 | (10) | 0.1<br>0.01 | 100<br>90 |
| 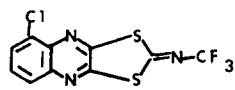 | (8) | 0.1<br>0.01 | 98<br>30 |
| 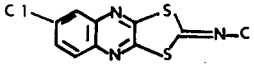 | (1) | 0.1<br>0.01 | 100<br>98 |
| 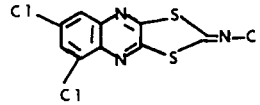 | (7) | 0.1<br>0.01<br>0.001 | 100<br>90<br>40 |
| 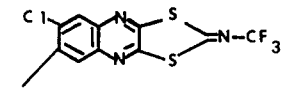 | (6) | 0.1<br>0.01 | 100<br>40 |
| 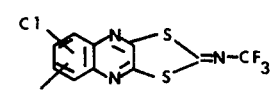 | | 0.1<br>0.01 | 100<br>90 |
| 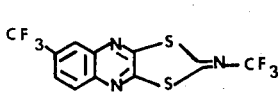 | (9) | 0.1<br>0.01<br>0.001 | 100<br>100<br>40 |

TABLE 1-continued (Mites which damage plants)
Tetranychus test (resistant)

| Active compounds | | Active compound concentration in % | Degree of destruction in % after 8 days |
|---|---|---|---|
| $O_2N$-quinoxaline-S-C=N-CF$_3$ structure | (11) | 0.1<br>0.01<br>0.001 | 100<br>90<br>40 |

EXAMPLE 2

Plutella Test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water, to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations, by weight, of the active compounds, the evaluation times and the results can be seen from the following table:

Table 2

(Insects which damage plants)
Plutella test

| Active compounds | | Active compound concentration in % | Degree of destruction in % after 3 days |
|---|---|---|---|
| quinoxaline-S-C=N-phenyl (known) | (A) | 0.1 | 20 |
| quinoxaline-S-C=N-CF$_3$ | (2) | 0.1<br>0.01 | 100<br>100 |
| 8-CH$_3$-quinoxaline-S-C=N-CF$_3$ | (4) | 0.1<br>0.01 | 100<br>50 |
| 6-CH$_3$-quinoxaline-S-C=N-CF$_3$ | (3) | 0.1<br>0.01 | 100<br>100 |
| Cl-quinoxaline-S-C=N-CF$_3$ | (1) | 0.1<br>0.01 | 100<br>100 |
| Cl,Cl-quinoxaline-S-C=N-CF$_3$ | (7) | 0.1<br>0.01 | 100<br>50 |
| Cl,Cl-quinoxaline-S-C=N-CF$_3$ | (6) | 0.1<br>0.01 | 100<br>100 |
| F$_3$C-quinoxaline-S-C=N-CF$_3$ | (9) | 0.1<br>0.01 | 100<br>100 |

EXAMPLE 3

Mycelium Growth Test

Nutrient medium used:
20 parts by weight of agar-agar
200 parts by weight of potato decoction
5 parts by weight of malt
15 parts by weight of dextrose 5 parts by weight of peptone
2 parts by weight of $Na_2HPO_4$
0.3 part by weight of $Ca(NO_3)_2$
Proportion of solvent to nutrient medium:

up to 7 slight inhibition of growth
9 growth equal to that of untreated control.

The active compounds, their concentrations and the results can be seen from the following table:

Table 3

| Mycelium growth test Active compounds | Active compound concentration, ppm | Test organisms | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Cl-quinoxaline-S-C(=N-CF3)-S (6) | 10 | 3 | 5 | 3 | 1 | 1 | 1 | 3 | 3 | 1 | 3 | 1 | 1 | 3 | 1 | 1 |
| F3C-quinoxaline-S-C(=N-CF3)-S (9) | 10 | 5 | — | — | — | 1 | 3 | 5 | 5 | 1 | — | 1 | 1 | 1 | 1 | 1 |
| H3CO-quinoxaline-S-C(=N-CF3)-S (10) | 10 | — | — | 1 | — | 2 | 3 | — | — | 1 | — | 3 | 5 | 1 | 1 | 1 |
| Cl-quinoxaline-S-C(=N-CF3)-S (1) | 10 | — | — | 1 | 1 | 1 | 1 | 3 | 5 | 1 | — | 1 | 3 | 1 | 1 | 1 |

1 Fusarium culmorum
2 Sclerotinia sclerotiorum
3 Fusarium nivale
4 Colletotrichum coffeanum
5 Rhizoctonia solani
6 Pythium ultimum
7 Cochliobolus miyabeanus
8 Verticillium alboatrum
9 Piricularia oryzae
10 Phialophora cinerescens
11 Helminthosporium gramineum
12 Mycosphaerella musicola
13 Phytophthora cactorum
14 Venturia inaequalis
15 Pellicularia sasakii 2 parts by weight of solvent mixture
100 parts by weight of agar nutrient medium
Composition of the solvent mixture:
0.19 part by weight of DMF or acetone
0.01 part by weight of emulsifier Emulvin W
1.80 parts by weight of water
2 parts by weight of solvent mixture The amount of active compound required for the desired concentration of active compound in the nutrient medium was mixed with the stated amount of solvent mixture. The concentrate was thoroughly mixed, in the stated proportion, with the liquid nutrient medium which had been cooled to 42°C. and was poured into Petri dishes of 9 cm diameter. Control plates to which the preparation had not been added were also set up.

When the nutrient medium had cooled and solidified, the plates were inoculated with the species of fungi stated in the table and incubated at about 21°C.

Evaluation was carried out after 4–10 days, dependent on the speed of growth of the fungi. When evaluation was carried out the radial growth of the mycelium on the treated nutrient media was compared with the growth on the control nutrient media. In the evaluation of the fungus growth, the following characteristic values were used:
1 no fungus growth
up to 3 very strong inhibition of growth
up to 5 medium inhibition of growth

EXAMPLE 4

Erysiphe Test

Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoreacearum*. The plants were subsequently placed in a greenhouse at 23°–24°C and at a relative atmospheric humidity of about 75%.

After 12 days, the infection of the cucumber plants was determined as a percentage of the untreated but also inoculated control plants. 0% means no infection; 100% means that the infection was exactly as great as in the case of the control plants.

The active compounds, the concentrations of the active compounds and the results can be seen from the following table:

Table 4

| Active compound | | Erysiphe test Infection in % of the infection of the untreated control at an active compound concentration of 0.025% by weight |
|---|---|---|
| 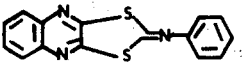 (known) | (A) | 100 |
| 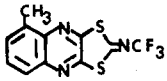 | (4) | 19 |
| 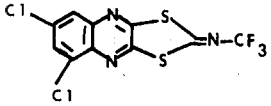 | (7) | 9 |

EXAMPLE 5

Podosphaera Test (powdery mildew of apples) [Protective]

Solvent: 4.7 parts by weight of acetone

Emulsifier: 0.3 part by weight of alkylaryl polyglycol ether

Water: 95 parts by weight

The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20°C and at a relative atmospheric humidity of 70%. They were then inoculated by dusting with conidia of the apple powdery mildew causative organism (*Podosphaera leucotricha* Salm.) and placed in a greenhouse at a temperature of 21°–23°C and at a relative atmospheric humidity of about 70%.

Ten days after the inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table:

Table 5

| Active compound | | Podosphaera test / protective Infection in % of the infection of the untreated control at an active compound concentration of 0.005 % by weight |
|---|---|---|
| 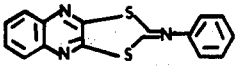 (known) | (5) | 100 |
| 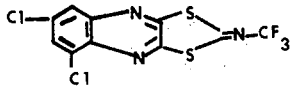 | (7) | 26 |
| 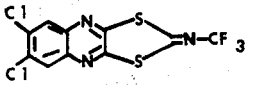 | (6) | 32 |

The process of the present invention is illustrated in the following preparative Examples.

EXAMPLE 6

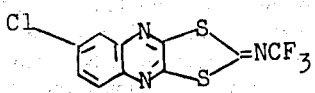 (1)

273 g (1.2 moles) of 2,3-dimercapto-6-chloro-quinoxaline were dissolved in 600 ml. of dry dimethylformamide. 245 g (2.4 moles) of triethylamine were added dropwise at 10°–15°C and 175 g (1.3 moles) of perfluoroazapropene were introduced into this suspension at 10°–25°C. After completion of the reaction, the mixture was further stirred for 45 minutes at room temperature and the reaction mixture was poured into approximately 4 kg of ice-water, while stirring. The precipitate which separated out was filtered off and dried. Extraction with 1 liter of carbon tetrachloride or methylene chloride and removal of the solvent gave 294 g (75%) of a yellow odorless powder of melting point 115°–120°C.

EXAMPLE 7

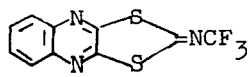

(2)

38.8 g (0.2 mole) of 2,3-dimercaptoquinoxaline were dissolved in 200 ml of dimethylformamide and 17 g (0.4 mole) of dry sodium fluoride were added. 30 g of perfluoroazapropene were introduced into this suspension at room temperature, at a moderate speed, so that as little gas as possible escaped. The reaction mixture was stirred further for approximately 30 minutes at room temperature and was then poured onto 500 g of ice. The precipitate which separated out was filtered off, dried, and extracted once with 200 ml of hot carbon tetrachloride or twice with 150 ml of hot cyclohexane at a time. After removing the solvent, 30 g (52%) of yellow crystals of melting point 157°–160°C were left.

EXAMPLE 8

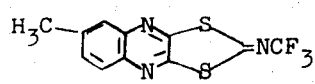

(3)

20.8 g (0.1 mole) of 6-methyl-2,3-dimercaptoquinoxaline were partially dissolved in 100 ml of dry dioxane, 9 g (0.2 mole) of dry sodium fluoride were added and 15 g (0.11 mole) of perfluoroazapropene were introduced slowly at 90°C, with good stirring, in such a way that no gas was evolved. After completion of the introduction, the reaction mixture was allowed to cool and was poured onto 300 g of ice and worked up in the manner indicated in Example 7. 13.5 g (45%) of yellow crystals of melting point 118°–120°C were obtained.

The compounds listed below can be prepared by methods analogous to those described in Examples 6 to 8:

| Compound No. | Formula | Melting point (°C) | Appearance |
| --- | --- | --- | --- |
| 4 | | 100 – 104 | yellow crystals |
| 5 | | 218 – 222 | yellow crystals |
| 6 | | 183 – 85 | yellow crystals |
| 7 | | 130 – 132 | yellow crystals |
| 8 | | 140 – 46 | yellow crystals |
| 9 | | 68 – 70 | yellow crystals |
| 10 | | 139 – 141 | yellow crystals |
| 11 | | 105 – 107 | yellow crystals |

Other compounds which can be similarly prepared include:

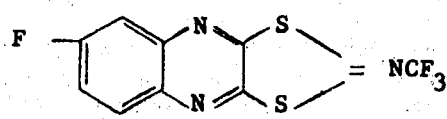

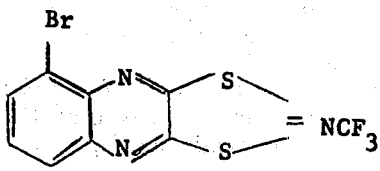

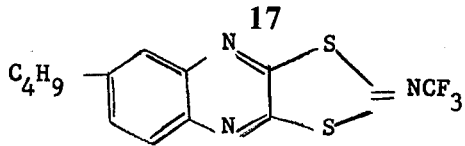

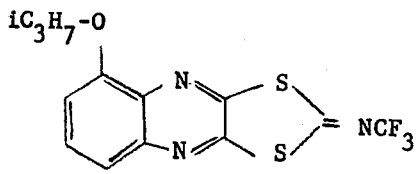

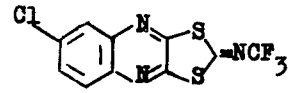

and the like.

It will be appreciated that the instant specification and examples are set forth by way of illustration and not limitation, and that various modifications and changes may be made without departing from the spirit and scope of the present invention.

What is claimed is:

1. A 2-trifluoromethylimino-1,3-dithiolo-quinoxaline of the formula

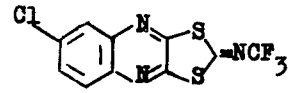

in which
each X is selected independently from the group of lower alkyl of up to 4 carbon atoms, lower alkoxy, trihalogenomethyl, trihalogenomethoxy, halogen and nitro, and
$n$ is 0, 1 or 2.

2. A compound according to claim 1, in which $n$ is 0, 1 or 2; and each X is selected independently from the group of methyl, methoxy, trifluoromethyl, trifluoromethoxy, fluorine, chlorine and nitro.

3. The compound according to claim 1 of the formula

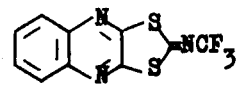

4. The compound according to claim 1 of the formula

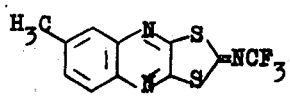

5. The compound according to claim 1 of the formula

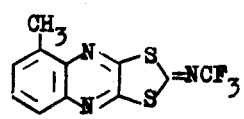

6. The compound according to claim 1 of the formula

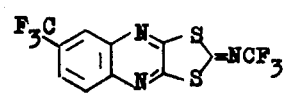

7. The compound according to claim 1 of the formula

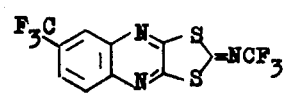

* * * * *